United States Patent [19]

Itoh et al.

[11] Patent Number: 5,086,133
[45] Date of Patent: Feb. 4, 1992

[54] PROCESS FOR PRODUCING HIGHLY WATER ABSORPTIVE POLYMER

[75] Inventors: Kiichi Itoh; Takeshi Shibano; Kenji Yoshinaga, all of Yokkaichi, Japan

[73] Assignee: Mitsubishi Petrochemical Company Limited, Tokyo, Japan

[21] Appl. No.: 703,047

[22] Filed: May 17, 1991

Related U.S. Application Data

[63] Continuation of Ser. No. 428,631, Oct. 30, 1989, abandoned, which is a continuation of Ser. No. 160,278, Feb. 25, 1988, abandoned.

[30] Foreign Application Priority Data

Feb. 27, 1987 [JP] Japan ................................ 62-44580

[51] Int. Cl.$^5$ .............................................. C08F 30/04
[52] U.S. Cl. ..................................... 526/93; 526/123; 526/200; 526/213; 526/217; 526/240; 526/306; 526/265
[58] Field of Search ................. 526/93, 123, 200, 213, 526/217, 240

[56] References Cited

U.S. PATENT DOCUMENTS

| | | | |
|---|---|---|---|
| 3,936,441 | 2/1976 | Holst et al. | 527/312 |
| 4,076,663 | 2/1978 | Masuda et al. | 527/312 |
| 4,093,776 | 6/1978 | Aoki et al. | 526/207 |
| 4,152,307 | 5/1979 | Shibahara et al. | 524/376 |
| 4,461,874 | 7/1984 | Teyssie et al. | 525/309 |
| 4,486,489 | 12/1984 | George | 526/240 |
| 4,525,527 | 6/1985 | Takeda et al. | 526/240 |
| 4,554,018 | 11/1985 | Allen | 526/240 |
| 4,703,067 | 10/1989 | Mikita et al. | 521/63 |

FOREIGN PATENT DOCUMENTS

| | | |
|---|---|---|
| 818653 | 7/1969 | Canada . |
| 85017328 | 8/1980 | Japan . |
| 55-133413 | 10/1980 | Japan ................. 526/240 |
| 58-15511 | 1/1983 | Japan ................. 526/240 |

*Primary Examiner*—Joseph L. Schofer
*Assistant Examiner*—N. Sarofim
*Attorney, Agent, or Firm*—Oblon, Spivak, McClelland, Maier & Neustadt

[57] ABSTRACT

There is provided a process for producing a highly water absorptive polymer, which comprises making up a mixture (A) comprising an aqueous solution of (a) a partially neutralized product of acrylic acid with 20% or more of carboxylic groups being neutralized to an alkali metal salt or ammonium salt, (b) a crosslinking agent having two or more copolymerizable vinyl groups in one molecule, (c) a basic vinyl monomer in a quantity of 20 mol % or less based on said partially neutralized product of acrylic acid, (d) a nonionic surfactant with HLB of 7 or more and (e) an oxidative radical polymerization initiator, said mixture (A) being maintained at a temperature of 50° C. or lower, and a mixture (B) comprising an amine or a reducing agent dissolved in water or in said mixture (A) from which at least the component (e) is removed, and mixing both the mixtures to cause polymerization.

21 Claims, No Drawings

PROCESS FOR PRODUCING HIGHLY WATER ABSORPTIVE POLYMER

This application is a continuation of application Ser. No. 428,631, filed on Oct. 30, 1989, now abandoned which is a continuation of Ser. No. 07/160,278 filed Feb. 25, 1988, now abandoned.

BACKGROUND OF THE INVENTION

1. Field of the Art

This invention is intended to provide a process for producing a highly water absorptive polymer having excellent water absorbing properties and high water absorbing rate with extreme ease and at low cost.

The polymer obtained according to the production process of the present invention can be swelled by absorption of a large amount of water within a short time and is insoluble in water, and has a great strength of the swelled gel, and therefore it can be used advantageously for production of various absorbing materials and various materials which are to be used under swelled state with water being absorbed.

2. Prior Art

Materials such as paper, pulp, nonwoven fabric, spongy urethane resins and the like have hitherto been used as water retentive materials for a variety of sanitary goods such as a sanitary napkin, paper diaper and the like and a variety of agricultural materials. However, these materials have a water absorption capacity of no more than 10-50 times their own weight, which causes problems that an extensively increased bulk of the material is required for absorbing or retaining a large amount of water and that water is easily released from the material in which water has been absorbed on pressing it.

There have recently been proposed a variety of highly water absorptive polymer materials and production methods thereof in order to settle the aforementioned problems of the water absorptive materials of this kind. For instance, there have been proposed a graft polymer of starch (Japanese Patent Publication No. 46199/78, etc.), a denaturated cellulose (Unexamined Published Japanese Patent Application No. 80376/75, etc.), a crosslinked water soluble polymer (Japanese Patent Publication No. 23462/68, etc.), a self-crosslinking polymer of an alkali metal salt of acrylic acid (Japanese Patent Publication No. 30710/79, etc.), crosslinked type polyacrylic acid alkali metal salt (Unexamined Published Japanese Patent Publication No. 71909/1983, Japanese Patent Publication No. 17328/1985), and a process for producing a crosslinked polyacrylic acid salt by means of an aqueous redox polymerization (Unexamined Published Japanese Patent Publication Nos. 71907/1983 and 18712/1984).

However, some of these highly water absorptive polymer materials have a number of problems in practical use or production on an industrial scale such that they are still insufficient in amount of water to be absorbed, with the gel strength after water absorption being small, and that the polymer obtained by drying is extremely hard and cannot be easily crushed thereby requiring a great mechanical crushing force. Also, some of those mentioned above employ a large amount of hydrocarbon type solvent, thus involving a serious problem on safety.

Further, as far as the present inventors know, most of the polymers obtained by the production processes described in the specifications mentioned above cause the so called "gel blocking" phenomenon when contacted with water, whereby water absorption with good efficiency cannot be effected, thus having the drawback of requiring long time for water absorption. Therefore, most of the polymers require a post-treatment step of surface crosslinking with a crosslinking agent such as polyglycidyl ether.

Moreover, in most of the production processes as mentioned above, the polymerization time or the treatment time in the above mentioned post-treatment is long and, in addition, the process is complicated, whereby productivity is poor, thus inevitably leading to increased cost.

SUMMARY OF THE INVENTION

The present invention is intended to overcome the above problems and provide a process for producing a highly water absorptive polymer excellent in water absorbing properties and having high water absorption rate within a very short time with good productivity, safely and at low cost.

The present inventors have made various studies in order to solve the above problems, and consequently found that a highly water absorptive polymer excellent in water absorbing properties, having high water absorption rate can be obtained safely within a very short time with good productivity, by polymerizing an aqueous solution of a partially neutralized product of acrylic acid containing as essential ingredients a small amount of a crosslinking agent, a basic vinyl monomer and a nonionic surfactant with HLB of 7 or more by the use of a redox type catalyst comprising an oxidative radical polymerization initiator and an amine or a reducing agent which are from separate sources of supply, preferably by practicing the polymerization on a movable belt in such a manner that the liquid layer formed on the belt will have a thickness of 10 mm or less. The present invention has been accomplished based on such finding.

Thus, the process for producing a highly water absorptive polymer according to the present invention comprises making up a mixture (A) comprising an aqueous solution of (a) a partially neutralized product of acrylic acid with 20% or more of carboxylic groups being neutralized to an alkali metal salt or ammonium salt, (b) a crosslinking agent having two or more copolymerizable vinyl groups in one molecule, (c) a basic vinyl monomer in a quantity of 20 mole % or less based on said partially neutralized product of acrylic acid, (d) a nonionic surfactant with HLB of 7 or more and (e) an oxidative radical polymerization initiator, said mixture (A) being maintained at a temperature of 50° C. or lower, and a mixture (B) comprising an amine or a reducing agent dissolved in water or in said mixture (A) from which at least the component (e) is removed, and mixing both the mixtures to cause polymerization.

A preferred embodiment of the present invention comprises, as mentioned above, mixing the mixture (A) and the mixture (B) on a movable belt or prior to feeding to a movable belt, and feeding the mixture onto the movable belt to a thickness of 10 mm or less, and causing polymerization on said belt.

The process for producing the highly water absorptive polymer of the present invention has such advantages that, in the first place, the polymer is very excellent in water absorbing ability thanks to the use of a specific crosslinking agent and a basic vinyl monomer; secondly, the polymer obtained is in the form of scales with increased specific surface area and therefore has high water absorption rate and can be readily crushed, since polymerization is carried out by use of a specific basic vinyl monomer and a nonionic surfactant with HLB of 7 or more, preferably on a movable belt while maintaining a thin liquid film state of 10 mm or less; thirdly, the polymerization time is extremely short due to the use of a specific redox catalyst for the polymerization initiator, and while most of prior art processes require as a post-treatment the step of surface crosslinking with polyglycidyl ether compound, etc. for improvement of water absorption rate, in the present invention, due to the use of a specific basic vinyl monomer and a surfactant as mentioned above, no such post-treatment is required, whereby the highly water absorptive polymer can be produced with very good productivity and at low cost; fourthly, according to the present invention, a hydrocarbon solvent having high combustibility such as hexane, cyclohexane, etc. is not used at all, and an acrylic acid type monomer, which has an excessive polymerizability, can be operated at a low temperature of 50° C. or lower whereby the oxidative radical initiator and reducing agent can be used as ones previously dissolved in the aqueous monomer solution, the instant process thus being very excellent in safety and operability.

Thus, the process for producing the highly water absorptive polymer according to the present invention is provided with high productivity, safety and economical advantages which have not been found in the prior art, and the polymer obtained has extremely high water absorbing ability and water absorbing rate. Accordingly, by making use of those properties, the instant process can be used advantageously not only for production of hygienic materials such as sanitary napkins, paper diapers, etc., but also for production of various materials for horticulture or agriculture, including soil improvers, water retention agents, etc.

DETAILED DESCRIPTION OF THE INVENTION

Partially neutralized product of acrylic acid

The partially neutralized product of acrylic acid to be used in the present invention comprises acrylic acid with 20% or more of carboxylic groups being neutralized to an alkali metal salt or ammonium salt.

As the alkali metal salt, sodium, potassium, lithium, rubidium salts, etc. may be included, and sodium salt or potassium salt is preferred in aspects of the performance of the polymer obtained, readiness in commercial availability, safety, etc.

In the case of a sodium salt or a potassium salt, it is preferable that 40 to 70% of the carboxylic groups of acrylic acid are neutralized to said alkali metal salt, and that the concentration of the partially neutralized product of acrylic acid obtained in the aqueous solution is less than 65% by weight. When the neutralization degree is less than 40% or over 70%, the resulting polymer has low water absorption ability, and also the gel having absorbed water will exhibit remarkably acidic or alkaline pH.

If the concentration of the neutralized product of acrylic acid in the aqueous solution is 65% or more, in order to maintain said concentration it is necessary to maintain the aqueous solution of the partially neutralized product of acrylic acid at a high temperature, say, 70° C. or higher. To maintain said monomer which has an extremely vigorous polymerizability at such high temperature is disadvantageous in view of operability and safety.

On the other hand, in the case of ammonium salt, it is preferable to use the neutralized product with 90% or more of the carboxylic groups of acrylic acid being neutralized. When the neutralization degree is less than 90%, the water absorption ability of the resulting polymer is low, and also the water-absorbed gel will exhibit slightly acidic pH.

For neutralization of acrylic acid monomer to an alkali metal salt or ammonium salt as described above, hydroxides, bicarbonates, etc. of alkali metals and ammonia can be used. Preferably used are hydroxides of alkali metals and ammonia Specific examples may include sodium hydroxide, potassium hydroxide and ammonium hydroxide.

Crosslinking agent

The crosslinking agent to be used in the production process of the present invention has two or more vinyl groups in the molecule, and must be one which is soluble in the aqueous solution of the partially neutralized product of acrylic acid and copolymerizable with said partially neutralized product of acrylic acid. Specific examples of such crosslinking agent may include ethylene glycol di(meth)acrylate, polyethylene glycol di(meth)acrylate, propylene glycol di(meth)acrylate, polypropylene glycol di(meth)acrylate, glycerin tri(meth)acrylate, tetramethylolmethane tetraacrylate, N,N'-methylenebis(meth)acrylamide, diallyl phthalate, diallyl maleate, diallyl terephthalate, triallyl cyanurate, triallyl isocyanurate, triallyl phosphate, etc. Among them, N,N'-methylenebis(meth)acrylamide, polyethylene glycol di(meth)acrylate and tetramethylolmethane tetraacrylate are particularly preferred.

The amount of these crosslinking agents used may be ordinarily 0.001 to 5 parts by weight, preferably 0.01 to 1 part by weight per 100 parts by weight of the partially neutralized product of acrylic acid. At a level less than 0.001 part by weight, while the water absorption ability of the polymer product can become extremely great, the water absorption rate and gel strength will become smaller. On the other hand, at a level exceeding 5 parts by weight, while the water absorption rate and gel strength can become extremely great, the water absorption ability becomes too low for a practical use.

Basic vinyl monomer

The basic vinyl monomer to be used in the present invention is a compound having a basic group such as primary amino group, secondary amino group, tertiary amino group, etc. or an amide group and a polymerizable vinyl group in one molecule. Specific examples may include (meth)acrylamide, N,N'-dimethyl(meth)acrylamide, dimethylaminopropyl(meth)acrylamide, dimethylaminoethyl (meth)acrylate, diethylaminoethyl (meth)acrylate, dimethylaminopropyl (meth)acrylate, 2-vinylpyridine, 4-vinylpyridine, etc. Among them, (meth)acrylamide and 2-vinylpyridine are particularly preferred in the present invention.

The amount of these basic vinyl monomers used may be ordinarily 20 mol % or less, preferably 10 mol % or less, based on the partially neutralized product of acrylic acid. The use in excess of 20 mol % of the monomer will remarkably lower the water absorption ability of the resulting polymer.

Surfactant

The surfactant usable in the present invention is a nonionic surfactant with HLB of 7 or more, and is required to be soluble in the aqueous solution of the partially neutralized product of acrylic acid.

Specific examples of such surfactants may include polyoxyethylene alkyl ethers, polyoxyethylene alkylphenol ethers, sorbitan fatty acid esters, polyoxyethylene sorbitan fatty acid esters, polyoxyethylene acyl esters, oxyethylene oxypropylene block copolymers, sucrose fatty acid esters, etc.

Among them, polyoxyethylene acyl esters are preferred in the present invention. Particularly preferred is polyethylene glycol dilaurate with HLB value of 10 or more.

The amount of these surfactants used may be generally 0.001 to 10 parts by weight, preferably 0.01 to 5 parts by weight, per 100 parts by weight of the partially neutralized product of acrylic acid. If it is less than 0.001 part by weight, no remarkable effect by addition thereof is exhibited, while if it exceeds 10 parts by weight, the water absorption rate and water absorption ability of the resulting polymer will be rather undesirably lowered.

Oxidative radical initiator

The oxidative radical initiator to be used in the production process of the present invention forms a redox system with a reducing agent, and must be a radical generating agent which is soluble in the aqueous solution of the partially neutralized product of acrylic acid and exhibits oxidizability. Examples of such oxidative agents may include (a) hydrogen peroxide, (b) persulfates such as ammonium persulfate, potassium persulfate, sodium persulfate, etc., (c) hydroperoxides such as tert-butyl hydroperoxide, cumene hydroperoxide, etc., and (d) secondary cerium salts, permanganates, chlorites, hypochlorites, and others.

Other water soluble radicals exhibiting no oxidizability, for example, azo compounds such as 2,2′-azobis(2-amidinopropane) dihydrochloride, which do not form a redox system with a reducing agent, are not used in the production process of the present invention.

The amount of these oxidative radical polymerization initiators used may be about 0.01 to 10% by weight, preferably 0.1 to 2% by weight based on the partially neutralized product of acrylic acid.

Amine or reducing agent

The amine or reducing agent to be used in the production process of the present invention is one which can form a redox system with the above oxidative radical polymerization initiator, and exhibit water solubility to some extent. Examples of such amines or reducing agents may include primary amines such as aniline, monoethanolamine, hexanemethylenediamine, etc., secondary amines such as diethanolamine, etc., sulfites such as sodium hydrogen sulfite, sodium sulfite, etc., sodium thiosulfate, cobalt acetate, cupric sulfate, ferrous sulfate, L-ascorbic acid, and L-ascorbic acid alkali metal salts such as sodium L-ascorbate, etc. Among these, in the present invention, L-ascorbic acid and L-ascorbic acid alkali metal salt have particularly large effect and therefore are preferred.

The amount of these amines or reducing agents used may be 0.001 to 10% by weight, preferably 0.01 to 2% by weight based on the partially neutralized product of acrylic acid.

Polymerization

An aqueous solution of starting polymerizable monomers is prepared by dissolving a crosslinking agent, a basic vinyl monomer and a nonionic surfactant with HLB of 7 or more in an aqueous solution of the partially neutralized product of acrylic acid, said aqueous solution of monomers being maintained at a temperature of 50° C. or lower, and an oxidative radical polymerization initiator is dissolved in said solution to make up a mixture (A), while on the other hand, in said aqueous solution of monomers, or water, or said aqueous solution of monomers which is further diluted with water, an amine or a reducing agent is dissolved to make up a mixture (B), and thereafter the mixture (A) and the mixture (B) are mixed to cause polymerization.

The term "to make up a mixture (A)" herein involves not only the case of preparing a single solution containing all of the solute components, but also the case in which plural solutions each containing only a part of the solute components have been previously prepared, and the solution (A) is prepared by mixing such solutions in situ where it is mixed with the mixture (B). Similarly, the mixture (B) is not necessarily limited to a single solution previously prepared.

Polymerization of the (A)/(B) mixture may be performed in a simple vessel, but it is preferable to employ a manner in which the mixture (A) and the mixture (B) are mixed on a movable belt or prior to feeding onto a movable belt, and the mixture is fed onto the movable belt to a thickness or 10 mm or less to carry out polymerization.

If the temperature of the aqueous solution of monomers becomes 50° C. or higher, said aqueous solution will become remarkably unstable and have an undesirable tendency to polymerization. Such tendency is marked when the oxidative radical polymerization initiator is dissolved in said solution.

According to a preferable manner, as mentioned above, polymerization is carried out on a movable belt by mixing the mixture (A) having the oxidative radical polymerization initiator dissolved therein and the mixture (B) containing an amine or a reducing agent, wherein various modes may be adopted for the mixing and polymerization. For example, the mixture (A) and the mixture (B) are mixed in a mixing tank equipped with a stirring blade or in a line using a stirring blade, and fed onto a movable belt to a thickness of 10 mm or less to carry out polymerization. In another mode, the mixture (A) is fed onto a movable belt to a thickness of 10 mm or less, and thereafter the mixture (B) is sprayed thereon through a spray nozzle to carry out polymerization.

The mixing ratio of the mixture (A) to the mixture (B) may vary widely depending on the mixing manner employed and the kind and composition of the solvent used for the amine or reducing agent in the mixture (B), etc., but generally (A):(B)=99:1 to 10:90 (% by volume). When water is used as the solvent for the mixture (B), the concentration of the monomers contained in the mixture (A) is lowered by the mixing. It is therefore preferable to make the proportion of the mixture (B) as low as possible.

The mixture of the mixture (A) and the mixture (B) is fed on a movable belt so that it will have a thickness of 10 mm or less. If the thickness becomes 10 mm or more, the polymer after polymerization will become a hard mass which cannot be easily crushed, which will ill affect the absorption rate. The polymerization atmosphere temperature is not particularly limited, but generally 20° to 100° C., preferably 30° to 50° C. The polymerization time is extremely short, namely several seconds to one hour, usually several seconds to one minute.

The type of the movable belt polymerization device to be used in the present invention is not particularly limited, provided that it can hold thereon the aqueous solution of monomers, etc. For instance, the endless belt type may be mentioned.

After completion of polymerization, the polymer obtained is scraped off from the belt, subjected to conventional drying procedure, and then crushed to obtain the product.

EXPERIMENTAL EXAMPLES

Example 1

A 10-liter flask was charged with 1050 g of sodium hydroxide (purity: 95% by weight), which was dissolved in water by addition of 2780 g of water under ice-cooling. To the solution, 3000 g of acrylic acid was gradually added under ice-cooling to effect neutralization. The neutralization degree was about 60%, and the concentration of the partially neutralized product of acrylic acid (acrylic acid +sodium acrylate) in the aqueous solution was about 52% by weight.

Subsequently, into the above aqueous solution of the partially neutralized product of acrylic acid, 15 g of N,N'-methylenebisacrylamide, 500 g of acrylamide and 3.2 g of polyethylene glycol dilaurate (HLB 14) were respectively dissolved to obtain an aqueous solution of starting monomers, which was maintained at 40° C. In 2000 g of the aqueous solution of starting monomers, 87 g of 31% aqueous solution of hydrogen peroxide was dissolved to prepare a mixture (A).

Separately, in 2000 g of the above aqueous solution of starting monomers, 11 g of L-ascorbic acid was dissolved to prepare a mixture (B).

The above mixtures (A) and (B) were respectively delivered by pumps at a rate of 100 cc/min. into a mixing tank which was equipped with a stirring blade so as to effect mixing with good efficiency within a very short time.

After carrying out mixing in the mixing tank, the mixture was fed onto an endless belt to a thickness of about 3 to 5 mm. Polymerization was initiated at about 3 seconds after feeding and completed within 10 seconds. The polymer obtained, which was a gel containing a slight amount of water, was collected by a scraper from the endless belt, and after drying could be easily crushed.

Example 2

A 10-liter flask was charged with 3111 g of a 45% aqueous solution of potassium hydroxide, into which was gradually added 3000 g of acrylic acid under ice-cooling to effect neutralization. The neutralization degree was about 60% and the concentration of the partially neutralized product of acrylic acid in the aqueous solution was about 64.6% by weight.

Subsequently, into the above aqueous solution of the partially neutralized product of acrylic acid, 4.5 g of N,N'-methylenebisacrylamide, 500 g of methacrylamide and 3.2 g of polyethylene glycol dilaurate (HLB=16) were respectively dissolved to obtain an aqueous solution of starting monomers, which was maintained at 40° C.

Next, in 2000 g of said aqueous solution of monomers, 48 g of 31% aqueous solution of hydrogen peroxide was dissolved to prepare a mixture (A).

Separately, in 2000 g of the above aqueous solution of starting monomers, 6 g of sodium L-ascorbate was dissolved to prepare a mixture (B).

The above mixtures (A) and (B) were respectively delivered by pumps at a rate of 100 cc/min. into a mixing tank which was equipped with a stirring blade so as to effect mixing with good efficiency within a very short time. After carrying out mixing in the mixing tank, the mixture was fed onto an endless belt to a thickness of about 3 to 5 mm. Polymerization was initiated at about 2 seconds after feeding and completed within 5 seconds.

The polymer obtained, which was a gel-like substance containing a slight amount of water, was collected by a scraper from the endless belt, and after drying could be easily crushed.

Example 3

A 10-liter flask was charged with 2690 g of 25% ammonia water, into which was gradually added 3000 g of acrylic acid to effect neutralization. The neutralization degree was about 95%, and the concentration of the partially neutralized product of acrylic acid in the aqueous solution was about 65% by weight.

Subsequently, in the above aqueous solution of the partially neutralized product of acrylic acid, 5.0 g of N,N'-methylenebisacrylamide, 25 g of 2-vinylpyridine and 3.2 g of polyethylene glycol dilaurate (HLB=14) were respectively dissolved to obtain an aqueous solution of the starting monomers, which was maintained at 40° C. In 2000 g of the aqueous solution of monomers, 87 g of 31% aqueous solution of hydrogen peroxide was dissolved to prepare a mixture (A).

Separately, in 2000 g of the above aqueous solution of the starting monomers, 11 g of L-ascorbic acid was dissolved to prepare a mixture (B).

The above mixtures (A) and (B) were respectively delivered by pumps at a rate of 150 cc/min. into a mixing tank which was equipped with a stirring blade so as to effect mixing with good efficiency within a very short time. After carrying out mixing in the mixing tank, the mixture was fed onto an endless belt to a thickness of about 2 to 4 mm. Polymerization was initiated at about 2 seconds after feeding and completed within 5 seconds.

The polymer obtained, which was a gel-like substance containing a slight amount of water, was collected by a scraper from the endless belt, and after drying could be easily crushed.

Example 4

The procedure set forth in Example 1 was repeated except for using 12 g of potassium sulfate in place of the 31% aqueous solution of hydrogen peroxide and 6.0 g of sodium hydrogen sulfite in place of L-ascorbic acid to obtain a dried polymer.

Example 5

The procedure set forth in Example 2 was repeated except for using 18.2 g of polyethylene glycol (MW =600) diacrylate in place of N,N'-methylenebisacrylamide to obtain a dried polymer.

Example 6

The procedure set forth in Example 2 was repeated except for using 11 g of tetramethylolmethane tetraacrylate in place of N,N'-methylenebisacrylamide to obtain a dried polymer.

Example 7

The procedure set forth in Example 2 was repeated except for using 8.5 g of triethanolamine in place of sodium L-ascorbate to obtain a dried polymer.

Example 8

An aqueous solution of the starting monomers was obtained in the same manner as in Example 2 and maintained at 40° C.

In 2000 g of the aqueous solution of monomers, 49 g of 31% aqueous solution of hydrogen peroxide was dissolved to prepare a mixture (A).

Separately, 23 g of L-ascorbic acid was dissolved in 500 g of water to prepare a mixture (B).

The above mixture (A) was fed by a pump at a rate of 300 cc/min. onto an endless belt to a thickness of 3 to 5 mm. Subsequently, the mixture (B) was sprayed on the mixture (A) at an amount of 10.6 cc/min. through a spray nozzle. Polymerization was initiated at about 3 seconds after spraying, and completed after 5 seconds.

The polymer which was obtained as a gel-like substance containing a slight amount of water could be easily collected by a scraper and easily crushed after drying.

Comparative Example 1

The procedure set forth in Example 2 was repeated except for not using methacrylamide to obtain a dried polymer.

Comparative Example 2

The procedure set forth in Example 2 was repeated except for not using polyethylene glycol dilaurate (HLB=16) to obtain a dried polymer.

Comparative Example 3

The procedure set forth in Example 3 was repeated except for not using 2-vinylpyridine to obtain a dried polymer.

For the polymers obtained in the above Examples and Comparative Examples, the following tests were conducted to evaluate water absorbing ability, water absorbing rate and gel blocking phenomenon. The results are shown in Table 1.

A. Water Absorbing Ability

About 1 g of the polymer and about 500 g of a saline solution having a concentration of about 0.9% by weight were respectively weighed and charged in one liter-beaker. After stirring, the beaker was left standing for 1 hour to have the polymer sufficiently swelled with the saline solution. Next, the beaker content was sufficiently drained through a 100 mesh filter, and the amount of the swelled gel was measured and the water absorbing ability was calculated according to the following formula:

$$\text{Water absorbing ability (g/g resin)} = \frac{\text{Weight of swelled gel (g)}}{\text{Charged amount of polymer (g)}}$$

B. Water Absorbing Rate

About 500 g of a saline solution having a concentration of 0.9% by weight was weighed and charged in one liter-beaker, and then about 1 g of the polymer was weighed and added to the saline solution to disperse therein. The beaker was left standing for a predetermined time (1 min., 3 min., 5 min.) to have the polymer swelled with the saline solution.

After draining the beaker content through a 100 mesh filter, the amount of the swelled gel was measured to determine the water absorbing ability per the above respective times according to the formula shown in A.

C. Gel Blocking Phenomenon 0.5 g of the polymer was sampled in a petri dish and 20 cc of 0.9% saline solution was added dropwise with a pipette, and occurrence of gel blocking phenomenon was observed visually.

TABLE 1

| Example No. | Water absorbing ability (g/g resin) | Water absorbing rate (g/g resin) | | | Gel blocking phenomenon |
|---|---|---|---|---|---|
| | | 1 min. | 3 min. | 5 min. | |
| Example | | | | | |
| 1 | 58.6 | 35.4 | 48.9 | 51.3 | none |
| 2 | 63.3 | 38.8 | 49.5 | 58.5 | none |
| 3 | 58.2 | 37.5 | 48.2 | 52.1 | none |
| 4 | 56.2 | 31.5 | 42.3 | 52.6 | none |
| 5 | 65.8 | 35.6 | 49.8 | 59.3 | none |
| 6 | 59.2 | 39.5 | 48.9 | 57.2 | none |
| 7 | 55.3 | 32.1 | 44.4 | 52.3 | none |
| 8 | 65.3 | 42.3 | 53.5 | 60.8 | none |
| Comparative Example | | | | | |
| 1 | 40.3 | 25.3 | 32.8 | 37.2 | none |
| 2 | 65.3 | 8.6 | 13.5 | 16.3 | observed |
| 3 | 34.6 | 25.4 | 28.8 | 31.5 | none |

What is claimed is:

1. A process for producing a highly water absorptive polymer, which comprises:
   preparing a mixture (A) comprising an aqueous solution of (a) a partially neutralized product of acrylic acid with 20% or more of carboxylic groups being neutralized to an alkali metal salt or ammonium salt, (b) a crosslinking agent having two or more copolymerizable vinyl groups in one molecule, (c) a basic vinyl monomer in a quantity of 20 mol % or less based on said partially neutralized product of acrylic acid, (d) a nonionic surfactant with HLB of 7 or more and (e) an oxidative radical polymerization initiator, said mixture (A) being maintained at a temperature of 50° C. or lower, and a mixture (B) comprising an amine or a reducing agent dissolved in water or in said mixture (A) from which at least the component (e) is removed; and mixing both the mixtures and conducting polymerization at a temperature of 30° to 50° C.

2. The process according to claim 1, wherein the mixture (A) and the mixture (B) are mixed on a movable belt or prior to feeding onto a movable belt, and fed onto the movable belt to a thickness of 10 mm or less to cause polymerization on said belt.

3. The process according to claim 1, wherein the partially neutralized product of acrylic acid (a) is one of which 40 to 70% of the carboxylic groups of the acrylic acid are neutralized to sodium salt and (or) potassium salt and the concentration of said partially neutralized product of acrylic acid in the aqueous solution is less than 65% by weight.

4. The process according to claim 3, wherein the partially neutralized product of acrylic acid (a) is obtained by neutralization of acrylic acid monomer with sodium hydroxide, potassium hydroxide or mixtures thereof.

5. The process according to claim 1, wherein the partially neutralized product of acrylic acid (a) is one of which 90% or more the carboxylic groups of the acrylic acid are neutralized to the ammonium salt.

6. The process according to claim 5, wherein the partially neutralized product of acrylic acid (a) is obtained by neutralization of acrylic acid monomer with ammonium hydroxide.

7. The process according to claim 1, wherein the crosslinking agent is selected from the group consisting of N,N'-methylenebis(meth)acrylamide, polyethylene glycol di(meth)acrylate and tetramethylolmethane tetraacrylate and mixtures thereof.

8. The process according to claim 1, wherein the amount of the crosslinking agent (b) used is 0.01 to 1 part by weight per 100 parts by weight of the partially neutralized product of acrylic acid (a).

9. The process according to claim 1, wherein the basic vinyl monomer (c) is selected from the group consisting of (meth)acrylamide, N,N'-dimethylmethacrylamide, dimethylaminoethyl(meth)acrylamide, 2-vinylpyridine and 4-vinylpyridine and mixtures thereof.

10. The process according to claim 1, wherein the nonionic surfactant (d) is a polyoxyethylene acyl ester.

11. The process according to claim 10, wherein the nonionic surfactant (d) is a polyethylene glycol dilaurate with HLB value of 10 or more.

12. The process according to claim 1, wherein the amount of the nonionic surfactant (d) used is 0.01 to 5 parts by weight per 100 parts by weight of the partially neutralized product of acrylic acid (a).

13. The process according to claim 1, wherein the oxidative radical initiator (e) is selected from the group consisting of (i) hydrogen peroxide, (ii) persulfates selected from ammonium persulfate, potassium persulfate and sodium persulfate, (iii) hydroperoxides selected from tert-butyl hydroperoxide and cumene hydroperoxide, and (iv) secondary cerium salts, permanganates, chlorites and hypochlorites.

14. The process according to claim 1, wherein the amount of the oxidative radical initiator (e) used is 0.1 to 2% by weight based on the partially neutralized product of acrylic acid (a).

15. The process according to claim 1, wherein the amine or reducing agent dissolved in the mixture (B) is selected from the group consisting of (i) a primary amine selected from aniline, monoethanolamine and hexanemethylenediamine, (ii) a secondary amine selected from diethanolamine, (iii) a sulfite selected from sodium hydrogen sulfite and sodium sulfite and (iv) sodium thiosulfate, cobalt acetate, cupric sulfate, ferrous sulfate, L-ascorbic acid and an alkali metal salt of L-ascorbic acid.

16. The process according to claim 1, wherein the amount of the amine or reducing agent used is 0.01 to 2% by weight based on the partially neutralized product of acrylic acid (a).

17. The process according to claim 1, wherein the oxidative radical polymerization initiator (e) is hydrogen peroxide and the reducing agent is L-ascorbic acid or an alkali metal salt of L-ascorbic acid.

18. The process according to claim 1, wherein the mixing ratio of the mixture (A) to the mixture (B) is 99:1 to 10:90 (% by volume).

19. The process according to claim 1, wherein the polymerization is carried out for several seconds to one minute.

20. A process for producing a highly water absorptive polymer, which comprises:
(A) preparing a mixture of an aqueous solution of (i) a partially neutralized product of acrylic acid with at least 20% of carboxylic groups being neutralized in the form of an alkali metal salt or an ammonium salt, (ii) a crosslinking agent having at least two copolymerizable vinyl groups in one molecule, (iii) a basic vinyl monomer in an amount of no more than 20 mol % based on said partially neutralized acrylic acid, (iv) a nonionic surfactant with an HLB value of at least 7 and (v) an oxidative radical polymerization initiator, said mixture being maintained at a temperature of no more than 50° C.;
(B) preparing a mixture of an amine or a reducing agent dissolved in water;
(C) mixing both of said mixtures in a vessel; and
(D) feeding said mixed solution from said vessel onto a movable belt to a thickness of no more than 10 mm in order to polymerize the polymerizable ingredients at a temperature of 30° to 50° C.

21. A process for producing a highly water absorptive polymer, which comprises:
(A) preparing a mixture of an aqueous solution of (i) a partially neutralized product of acrylic acid with at least 20% of carboxylic groups being neutralized in the form of an alkali metal salt or an ammonium salt, (ii) a crosslinking agent having at least two copolymerizable vinyl groups in one molecule, (iii) a basic vinyl monomer in an amount of no more than 20 mol % based on said partially neutralized acrylic acid, (iv) a nonionic surfactant with an HLB value of at least 7 and (v) an oxidative radical polymerization initiator, said mixture being maintained at a temperature of no more than 50° C.;
(B) preparing a mixture of an amine or a reducing agent dissolved in water;
(C) feeding said neutralized acrylic acid containing mixture onto a movable belt to a thickness of no more than 10 mm; and thereafter
(D) spraying the mixture containing the reducing agent onto the material on said movable belt thereby conducting polymerization of the polymerizable ingredients at a temperature of 30° to 50° C.

* * * * *